(12) United States Patent
Colin

(10) Patent No.: US 6,175,029 B1
(45) Date of Patent: Jan. 16, 2001

(54) METHOD FOR OBTAINING ORGANOSILANES USING A DISTRIBUTION REACTION

(75) Inventor: Pascale Colin, Chassieu (FR)

(73) Assignee: Rhodia Chimie, Courbevoie Cedex (FR)

( * ) Notice: Under 35 U.S.C. 154(b), the term of this patent shall be extended for 0 days.

(21) Appl. No.: 09/381,658

(22) PCT Filed: Mar. 26, 1998

(86) PCT No.: PCT/FR98/00610

§ 371 Date: Nov. 30, 1999

§ 102(e) Date: Nov. 30, 1999

(87) PCT Pub. No.: WO98/43984

PCT Pub. Date: Oct. 8, 1998

(30) Foreign Application Priority Data

Mar. 27, 1997 (FR) .................................................. 97 04018

(51) Int. Cl.⁷ ....................................................... C07F 7/08
(52) U.S. Cl. .............................................................. 556/469
(58) Field of Search ................................................ 556/469

(56) References Cited

U.S. PATENT DOCUMENTS

| 4,889,838 | * | 12/1989 | Lewis et al. | ..................... 556/469 X |
| 5,493,043 | * | 2/1996 | Marko | .................................. 556/469 |

FOREIGN PATENT DOCUMENTS

| 0 147 834 | 7/1985 | (EP) . |
| 0 743 315 | 11/1996 | (EP) . |
| 2 119 477 | 8/1972 | (FR) . |

* cited by examiner

*Primary Examiner*—Paul F. Shaver
(74) *Attorney, Agent, or Firm*—Burns, Doane, Swecker & Mathis, L.L.P.

(57) ABSTRACT

A redistribution reaction between organohydrochlorosilanes and optionally chlorinated organosilanes is run in the presence of a catalyst in the solid state which comprises an alumina with an alkali metal or alkaline earth metal content expressed in ppm of the corresponding oxides of less than or equal to 500 ppm.

16 Claims, No Drawings

METHOD FOR OBTAINING ORGANOSILANES USING A DISTRIBUTION REACTION

The subject of the present invention is an improved process for obtaining organosilanes and it relates in particular to an improved process for obtaining organosilanes in which a so-called redistribution reaction is involved. More particularly, the present invention relates to an improved process for obtaining organosilanes, involving a redistribution reaction between a chlorinated organohydrosilane and an organo-substituted and optionally chlorinated silane to give a product comprising a redistributed chlorinated organohydrosilane which is extracted from the reaction medium by distillation.

Without limitation, the present invention is aimed quite especially at a redistribution reaction between an alkylhydrodichlorosilane and a trialkylchlorosilane to give a product comprising a redistributed dialkylhydrochlorosilane. This redistributed dialkylhydrochlorosilane is a synthesis reagent which is highly prized in a great many and varied applications, examples being the preparation of organosilicon monomers or more condensed base compounds.

The dialkylhydrochlorosilane is one of the by-products of the synthesis of alkylchlorosilanes in accordance with a conventional and well-known procedure which consists in reacting alkyl chloride with silicon in the presence of a copper catalyst to form alkylchlorosilanes. In this synthesis, the dialkyldichlorosilane is the main product. In addition to the dialkylhydrochlorosilane by-product specified above, compounds of the trialkylchlorosilane, alkyltrichlorosilane and alkylhydrodichlorosilane type are also obtained.

In view of the industrial interest of these products in the chemistry of silicones and especially of dialkylhydrochlorosilanes such as dimethylhydrochlorosilane, numerous proposals have seen the light of day for methods of obtaining these by-products. One of the few proposals which has proved itself in this respect is that which consists in carrying out a redistribution reaction between, for example, an alkylhydrodichlorosilane and a trialkylchlorosilane or between an alkylhydrodichlorosilane and a tetraalkylsilane. This redistribution leads to the specified dialkylhydrochlorosilanes which are extracted from the reaction medium by distillation.

In this context, numerous redistribution reactions of organosilanes, which cut and redistribute the silicon-alkyl, silicon-chlorine and/or silicon-hydrogen bonds, in the presence of various catalysts such as Lewis acids, are known. French Patent FR-A-2 119 477 is a good illustration of this technique for preparing dialkylhydrochlorosilanes by redistribution/distillation. In accordance with the teaching of this patent, methylhydrodichlorosilane and trimethylchlorosilane are reacted in a molar ratio of methylhydrodichlorosilane to trimethylchlorosilane of the order of 0.5 and in the presence of a catalyst consisting of $AlCl_3$. The reaction mixture is placed in a reactor under an autogenous pressure of the order of 3 to $5 \times 10^5$ Pa and is held for several hours at a temperature of the order of 85 to 170° C. The Applicant has repeated this prior art method and has observed that it involves a reaction in homogeneous catalysis in which the reacting substances and the catalyst form a single liquid phase. After the redistribution reaction has been implemented, the redistributed dimethylhydrochlorosilane is separated from the reaction mixture by distillation and, at the end of the distillation step, a distillation residue comprising the catalyst is left. The said residue is generally in the form of a suspension, since a greater or lesser proportion of the catalyst (which will depend on the amount employed at the start) is in the solid state in the residue. At the end of the process, owing to the dual state of the catalyst (solid state and dissolved state), the separation of $AlCl_3$ is made difficult, which considerably complicates the implementation of the process, and it is therefore quicker to destroy the catalyst by conducting an acidic or basic hydrolysis of the distillation residue. It must, however, be borne in mind that results of this kind are not satisfactory from the standpoint of industrial profitability: the aluminium chloride cannot be recycled, owing to its hydrolysis, and, furthermore, it presents the problem of aqueous effluents which can be awkward.

In the light of this knowledge, one of the essential objectives of the present invention consists in the development of a novel process for obtaining organosilanes which involves a heterogeneously catalysed redistribution reaction between a chlorinated organohydrosilane and an organo-substituted and optionally chlorinated silane. This novel process must employ a catalyst which remains in the solid state in the presence of the reacting substances and must lead, at the end of the reaction, to a reaction medium comprising a solid phase, the catalyst, which can easily be recycled in its entirety into a new operation, and a liquid phase comprising a redistributed chlorinated organohydrosilane which is recovered in conventional manner by distillation (for example).

Another essential objective of the invention is to provide a process of the type specified above which is particularly simple to implement and economic.

These various objectives are achieved by the implementation of the process according to the invention, which involves the use of an effective amount of an alumina-based catalyst.

The document EP-A-0 743 315 proposed a process for redistributing a mixture of methylsilanes by heterogeneous catalysis over alumina for the purpose of increasing the dimethylhydrochlorosilane and/or trimethylchlorosilane concentration of the said mixture. The starting materials referred to in this prior art relate only to mixtures of methylchlorosilanes (approximately 5 in number) and tetramethylsilane having low boiling points (methylsilanes boiling between 35 and 70° C. under atmospheric pressure are involved) as are separated by distillation of the crude mixture obtained from the direct Rochow synthesis, which consists in reacting methyl chloride over a catalyst mass composed of silicon and a catalyst. This prior art says absolutely nothing about the possibility of employing heterogeneous catalysis over alumina to aid a specific redistribution reaction, as implemented in the process according to the invention, in which two pure organosilanes, separated beforehand from their preparation medium and consisting of a chlorinated organohydrosilane and an organo-substituted and optionally chlorinated silane, are brought into contact.

The merit of the Applicant was not limited to this demonstration of the possibility of employing heterogeneous catalysis over alumina in order to promote a specific redistribution reaction between two organosilanes taken in the pure state. In fact, entirely surprisingly, the Applicant also found that the alumina must meet well-defined characteristics in order to perform correctly its role of heterogeneous catalyst in a specific redistribution reaction.

The present invention therefore provides a process for obtaining organosilanes, comprising a redistribution reaction between a chlorinated organohydrosilane of formula (1) $(R)_a(H)_bSiCl_{4-a-b}$ and an organo-substituted and optionally chlorinated silane of formula (2) $(R')_cSiCl_{4-c}$, in which formulae a 1 or 2, b=1 or 2, a+b≦3, c=1, 2, 3 or 4, the symbols R and R' are identical or different and each represent a linear or branched $C_1$–$C_6$ alkyl radical or a $C_6$–$C_{12}$ aryl radical, the said redistribution reaction proceeding in the presence of an effective amount of a catalyst based on a metal derivative, and the said process being characterized in that the catalyst remains in the solid state in the presence of the reacting silanes (1) and (2) and consists of an alumina which has an alkali metal M or alkaline earth metal M' content, expressed in ppm of oxide $M_2O$ or M'O relative to the weight of catalyst (alumina comprising in particular M or M'), of less than or equal to 500 ppm.

In accordance with one preferred embodiment of the invention, the alumina used has an alkali metal or alkaline earth metal content of less than or equal to 300 ppm, preferably less than or equal to 100 ppm.

Owing to the major processes for their manufacture, the aluminas employed in the present process usually contain sodium, the content of which will therefore be expressed in ppm of $Na_2O$ relative to the weight of alumina.

The Applicant notes that the alumina employed in its process, having an alkali metal or alkaline earth metal content within the abovementioned ranges, may advantageously comprise in its structure, in addition, a doping entity consisting of at least one halogen atom (such as, for example, a chlorine atom) and/or of at least one atom of a metal selected from the group of the elements of groups 5b and 6b and mixtures thereof (such as, for example, niobium, molybdenum and tungsten), with the proviso that the doping entity content, when it is present, and expressed in % by weight of halogen atom(s) and/or metal atom(s) relative to the weight of catalyst (alumina comprising the doping entity), is less than or equal to 50%, preferably less than or equal to 30% and, more preferably, is within the range from 0.1 to 20%.

For the definition of the elements of groups 5b and 6b, reference is made to the Periodic Classification of the Elements as published in "Handbook of Chemistry and Physics", 51st edition, 1970–1971, edited by "The Chemical Rubber Co.".

According to an even more preferred embodiment of the invention, the alumina used not only has an alkali metal or alkaline earth metal content and, if appropriate, a doping entity content which are within the abovementioned ranges but also possesses:
(i) a BET specific surface area greater than or equal to 50 m²/g, and
a total pore volume greater than or equal to 15 ml/100 g;
(ii) preferably
a BET specific surface area greater than or equal to 80 m²/g, and
a total pore volume ranging from 20 to 120 ml/100 g;
(iii) and still more preferably,
a BET specific surface area ranging from 100 to 600 m²/g, and
a total pore volume ranging from 25 to 80 ml/100 g.

The BET specific surface area is the specific surface area determined by nitrogen adsorption in accordance with the standard ASTM D 3663-78 established on the basis of the Brunauer-Emmett-Teller method described in "The Journal of the American Society" 60, 309 (1938).

The total pore volume (TPV) is measured as follows: the value of the grain density (Dg) and of the absolute density (Da) is determined using the method of pyknometry, employing mercury in the case of the grain density and helium in the case of the absolute density; the TPV is given by the formula:

$$TPV = \frac{1}{Dg} - \frac{1}{Da}$$

The alumina-based catalyst can be employed in various forms, such as powder, beads, comminuted forms, extrudates or residues, in which case shaping can optionally be carried out with the aid of a binder.

The alumina powder can be obtained by conventional methods, in particular by rapid dehydration of a hydrated alumina or of an aluminium hydroxide which is in the form, for example, of hydrargillite. In particular, the aluminas employed in the present process can be prepared by contacting a hydrated alumina in finely divided form with a stream of hot gas at a temperature of between 400° C. and 1000° C., then maintaining contact between the hydrate and the gases for a period ranging from a fraction of a second to 10 seconds (a step known as "flashing") and, finally, separating the partially dehydrated alumina and the hot gases. Reference may be made, in particular, to the process described in the American patent U.S. Pat. No. 2,915,365.

It is also possible to carry out autoclaving of the alumina agglomerates obtained beforehand, in an aqueous medium and, optionally, in the presence of acid, at a temperature of more than 100° C. and, preferably, of between 150° C. and 250° C. for a period which is preferably between 1 and 20 hours and then to dry them and calcine them.

The temperature and the duration of the calcination are regulated such that the specific surface areas obtained are within the abovementioned ranges.

The alumina can also be in the form of beads obtained from shaping by an oil-drop (or drop coagulation) technique. This type of beads can be prepared, for example, by a technique in accordance with the teaching of the patents EP-A-0 015 801 or EP-A-0 097 539. The porosity can be controlled, in particular, in accordance with the technique described in the patent EP-A-0 097 539, by drop coagulation of a suspension or of an aqueous dispersion of alumina or of a solution of basic aluminium salt which is present in the form of an emulsion consisting of an organic phase, an aqueous phase and a surfactant or emulsifier. The said organic phase can, in particular, be a hydrocarbon.

The alumina may also be present in one of its comminuted forms. These comminuted forms can be obtained from the comminution of any type of substance based on alumina, such as, for example, beads obtained by any type of technique (oil drop, film coater or rotating drum) or extrudates. The porosity of these comminuted forms is controlled by the choice of substance based on alumina which is comminuted in order to obtain them.

The alumina may also be in the form of extrudates. The latter can be obtained by grinding followed by extrusion of a substance based on alumina, the said substance possibly resulting from the rapid dehydration of hydrargillite or from the precipitation of an alumina gel. The porosity of these extrudates can be controlled by the choice of alumina employed and by the conditions under which this alumina is prepared or by the conditions under which this alumina is ground before extrusion. The alumina can also be mixed with pore-forming agents during grinding. By way of example, the extrudates can be prepared by the technique described in the patent U.S. Pat. No. 3,856,708.

In the case where the alumina is doped with one or more elements, the said doping can be carried out by any method known to the person skilled in the art. It can be carried out, for example, by impregnating the alumina-based support with one or more precursors of these elements or by mixing the precursor or precursors with the alumina during the shaping of this substance.

In the case of doping, for example, by impregnation, this is done in a known manner by contacting the support with a solution, a salt and/or a gel comprising at least one element in oxide form, in salt form or in the form of one of their precursors. The support can subsequently be subjected to an operation of drying and, optionally, of calcining; for example, the catalyst can be calcined at a temperature of between 150 and 1000° C., preferably between 200 and 900° C.

In the case of specific doping with a halogen, the precursor selected will be a halogen-containing mineral acid and, preferably, an organic halogen compound.

The catalyst is used in proportions by weight which range in general from 0.1 to 10% and, preferably, from 0.5 to 5% relative to the total weight of the silanes of formulae (1) and (2) introduced at the beginning. Proportions by weight to which special preference is given are those ranging from 0.8 to 2% relative to the same reference.

The temperature at which the redistribution reaction is implemented is generally greater than or equal to 130° C. The contact time between the silanes of formulae (1) and (2) and the alumina is not critical and may vary within wide ranges depending, in particular, on the apparatus, the stoichiometry of the reaction, and the chosen temperature.

Preferred temperature and contact time conditions are as follows: temperatures ranging from 140° C. to 260° C. and contact times ranging from 15 minutes to 8 hours. More preferred conditions are as follows: temperatures ranging from 150° C. to 240° C. and contact times ranging from 30 minutes to 5 hours.

From a practical standpoint, the process is conducted in a standard, closed reactor, which enables the liquid and/or gases to be contacted with a heterogeneous catalyst while operating under autogenous pressure. The process can be implemented batchwise or continuously: in the first variant, there is no constraint regarding the employment of the reactants and of the catalyst, which can without disadvantage be provided, in particular, in suspension in a liquid phase; in the other variant, the redistribution reaction can advantageously be conducted continuously in a reactor, in particular a tube reactor, comprising the solid catalyst arranged, for example, in a fixed or agitated bed.

Pressure is not a critical parameter of the process according to the invention. It is therefore possible to operate under pressures ranging from 2 to 50×10$^5$ Pa.

At the end of the heating period, when the redistribution reaction has taken place (monitoring, for example, of the level of target chlorinated organohydrosilane from redistribution), the reaction medium is cooled to a temperature less than 40° C., preferably of between 10 and 30° C., and is then returned to atmospheric pressure, carrying out a degassing operation if required. This produces a liquid phase, which is separated from the solid catalyst phase comprising the chlorinated organohydrosilane from redistribution, which can be recovered in conventional manner, for example, by distillation under atmospheric pressure.

As far as the two types of silane which are introduced for reaction is concerned, namely the chlorinated organohydrosilane of formula (1) and the organo-substituted and optionally chlorinated silane of formula (2), it will be noted that the symbols R and R' can be selected, for example, from the radicals methyl, ethyl, propyl, isopropyl, butyl, hexyl, phenyl, naphthyl and biphenylyl.

Preferably, the symbols R and R' are identical or different and each represent a linear or branched $C_1$–$C_3$ alkyl radical or a phenyl radical.

In any case, the symbols R and R' which are especially preferred are identical or different and each represent a methyl or a phenyl.

The process according to the present invention also applies to the implementation of a redistribution reaction between the chlorinated organohydrosilane (1) of formula $RHSiCl_2$ and the organo-substituted and chlorinated silane (2) of formula $R'_3SiCl$ (in this case a=1, b=1 and c=3), in which formulae the symbols R and R' have the general meanings given above, in the presentation of the invention, with respect to formulae (1) and (2).

The process according to the present invention applies particularly to the implementation of a redistribution reaction between the chlorinated organohydrosilane (1) of formula $RHSICl_2$ and the organo-substituted and chlorinated silane (2) of formula $R'_3SiCl$ (in this case a=1, b=1 and c=3) in which formulae the symbols R and R' are identical or different and each represent a linear or branched $C_1$–$C_3$ alkyl radical or a phenyl radical.

The process according to the present invention applies especially to the implementation of a redistribution reaction between the chlorinated organohydrosilane (1) of formula $RHSiCl_2$ and the organo-substituted and chlorinated silane (2) of formula $R'_3SiCl$, in which formulae the symbols R and R' are identical or different and each represent a methyl radical (abbreviated Me) or phenyl.

In general terms, in carrying out the process according to the present invention, the reactant of chlorinated organohydrosilane type of formula (1) can be present in the medium of the redistribution reaction in a proportion of at least 10 mol % relative to the mixture of chlorinated organohydrosilane of formula (1)+organo-substituted and optionally chlorinated silane of formula (2).

Preferably, the molar ratio

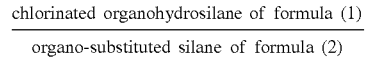

is between 0.1 and 2. More preferably still, this molar ratio is between 0.3 and 0.7.

In the context of the redistribution reaction to whose implementation the process according to the invention applies especially, involving, for example, $MeHSiCl_2$ and $Me_3SiCl$ as starting silanes (1) and (2), a chlorinated organohydrosilane is finally recovered which is produced by redistribution and consists of $Me_2HSiCl$ and the compound $Me_2SiCl_2$.

The examples which follow will make it possible to understand better all of the embodiments and advantages (processability) of the process according to the invention by emphasizing, by means of comparative tests, the small amount of $Me_2HSiCl$ formed (percentage by mass less than 5%) when the alumina employed does not correspond to the features according to the invention.

EXAMPLES 1 to 3 AND COMPARATIVE TESTS
A to C

The process is carried out batchwise in a 75 ml cylindrical reactor made of Hastelloy (a known material based on nickel) which is arranged vertically, is agitated by shaking and is equipped with heating means and with ports appropriate for the entry of a gas flow and for the introduction of the reactants and catalyst.

The interior of the reactor is first of all subjected to a stream of argon for 5 minutes and then charged in succession with 0.5 g of catalyst, in the form of a powder whose characteristics are indicated in Table I below, and 48 g of a mixture formed of $Me_3SiCl$ (313 g) and $MeHSiCl_2$ (16.7 g) so as to give a molar ratio of $MeHSiCl_2/Me_3SiCl$ of 0.5.

TABLE I

| Alumina | Na₂O ppm | Doping entity Type | Doping entity % | Specific surface area m²/g | Total pore volume ml/100 g |
|---|---|---|---|---|---|
| 1 | 5 | — | — | 408 | 39 |
| 2 | 30 | Cl | 1 | 210 | 60 |
| 3 | 30 | — | — | 210 | 60 |
| 4 | 730 | — | — | 244 | 50 |
| 5 | 1200 | — | — | 171 | 55 |
| 6 | 4000 | — | — | 210 | 59 |

The reactor is closed, agitation is commenced, and the reactor is heated at 160° C. for 4 hours.

At the end of this period, the reactor is cooled by quenching in an ice/water mixture for 5 minutes so as to bring its contents to a temperature of 20° C. It is then opened and the final reaction mixture is recovered, the liquid phase of the said mixture being analysed by gas chromatography using a Varian instrument equipped with a catharometer detector. The results obtained are reported in Table 2 below.

TABLE II

| | | Percentages by mass | | | |
|---|---|---|---|---|---|
| Examples | Catalyst | Me3 | MeH | Me2 | Me₂H |
| Ex. 1 | Alumina 1 | 48.5 | 5.0 | 33.3 | 8.2 |
| Ex. 2 | Alumina 2 | 48.0 | 3.2 | 33.0 | 7.9 |
| Ex. 3 | Alumina 3 | 53.9 | 4.9 | 30.9 | 5.9 |
| Compar. Ex. A | Alumina 4 | 59.2 | 14.4 | 17.0 | 2.5 |
| Compar. Ex. B | Alumina 5 | 65.1 | 27.4 | 3.6 | 0.3 |
| Compar. Ex. C | Alumina 6 | 64.0 | 26.7 | 6.1 | 0.1 |

Me3=Me₃SiCl; MeH=MeHSiCl₂; Me2=Me₂SiCl₂; Me2H=Me₂HSiCl

EXAMPLE 4

Example 2 is repeated but this time heating the reactor at 220° C. for 4 hours. The results obtained are compiled in Table III below.

TABLE III

| | | Percentages by mass | | | |
|---|---|---|---|---|---|
| Example | Catalyst | Me3 | MeH | Me2 | Me₂H |
| 4 | Alumina 2 | 40.4 | 2.5 | 40.1 | 13.5 |

What is claimed is:

1. Process for obtaining organosilanes, comprising a redistribution reaction between a chlorinated organohydrosilane of formula (1) $(R)_a(H)_bSiCl_{4-a-b}$ and an organo-substituted and optionally chlorinated silane of formula (2) $(R')_cSiCl_{4-c}$, in which formulae a=1 or 2, b=1 or 2, a+b≦3, c=1, 2, 3 or 4, the symbols R and R' are identical or different and each represent a linear or branched $C_1$–$C_6$ alkyl radical or a $C_6$–$C_{12}$ aryl radical, said redistribution reaction proceeding in the presence of an effective amount of a catalyst based on a metal derivative, wherein said catalyst remains in the solid state in the presence of the reacting silanes (1) and (2) and comprises an alumina which has an alkali metal M or alkaline earth metal M' content, expressed in ppm of oxide $M_2O$ or M'O relative to the weight of catalyst (alumina comprising in particular M or M'), of less than or equal to 500 ppm.

2. Process according to claim 1, wherein the alumina used has an alkali metal or alkaline earth metal content of less than or equal to 300 ppm.

3. Process according to claim 2, wherein the alkali metal or alkaline earth metal content is less than or equal to 100 ppm.

4. Process according to claim 1, wherein the alumina used comprises in its structure, in addition, a doping entity comprising at least one halogen atom and/or of at least one atom of a metal selected from the group of the elements of groups 5b and 6b and mixtures thereof, with the proviso that the doping entity content, expressed in % by weight of halogen atom(s) and/or metal atom(s) relative to the weight of catalyst (alumina comprising the doping entity), is less than or equal to 50%.

5. Process according to claim 4, wherein the doping entity content is less than or equal to 30%.

6. Process according to claim 5, wherein the doping entity content is within the range from 0.1 to 20%.

7. Process according to claim 1, wherein the alumina possesses:

a BET specific surface area greater than or equal to 50 m²/g, and a total pore volume greater than or equal to 15 ml/100 g.

8. Process according to claim 7, wherein the alumina possesses:

a BET specific surface area greater than or equal to 80 m²/g, and a total pore volume ranging from 20 to 120 ml/100 g.

9. Process according to claim 8, wherein the alumina possesses:

a BET specific surface area ranging from 100 to 600 m²/g, and a total pore volume ranging from 25 to 80 ml/100 g.

10. Process according to claim 1, wherein, the catalyst is used in proportions by weight which range from 0.1 to 10% relative to the total weight of the silanes of formulae (1) and (2) introduced at the beginning.

11. Process according to claim 10, wherein the proportions by weight range from 0.5 to 5%.

12. Process according to claim 1, wherein the temperature at which the redistribution reaction is implemented is greater than or equal to 130° C.

13. Process according to claim 12, wherein the temperature is within the range from 140 to 260° C.

14. Process according to claim 1, wherein, in relation to the two types of silane which are introduced for reaction, namely the chlorinated organohydrosilane of formula (1) and the organo-substituted and optionally chlorinated silane of formula (2), the symbols R and R' are identical or different and each represent a linear or branched $C_1$–$C_3$ alkyl radical or a phenyl radical.

15. Process according to claim 1, wherein a redistribution reaction is carried out between the chlorinated organohydrosilane (1) of formula $RHSiCl_2$ and the organo-substituted and chlorinated silane (2) of formula $R'_3SiCl$ (in this case a=1, b=1 and c=3).

16. Process according to claim 1, wherein the molar ratio $$\frac{\text{chlorinated organohydrosilane of formula (1)}}{\text{organo-substituted silane of formula (2)}}$$

is between 0.1 and 2.

* * * * *